United States Patent [19]
Sucher

[11] Patent Number: 6,106,819
[45] Date of Patent: Aug. 22, 2000

[54] METHODS OF TREATING HEADACHE AND FUNCTIONAL EXTRAOCULAR AND INTRAOCULAR MYOTENDINITIS

[76] Inventor: David F. Sucher, 10 Casa Vieja, Orinda, Calif. 94563

[21] Appl. No.: 08/999,782

[22] Filed: Dec. 5, 1997

Related U.S. Application Data

[60] Provisional application No. 60/034,103, Dec. 31, 1996, and provisional application No. 60/038,085, Feb. 18, 1997.

[51] Int. Cl.[7] .................................................. A61K 31/74
[52] U.S. Cl. ........................................................ 424/78.04
[58] Field of Search .......................... 424/78.04; 514/912

[56] References Cited

U.S. PATENT DOCUMENTS 5,776,445   7/1998   Cohen et al. ........................ 424/78.04

*Primary Examiner*—Carlos Azpuru
*Attorney, Agent, or Firm*—Harris Zimmerman

[57] ABSTRACT

Methods of treating headache and functional extraocular and intraocular myotendinitis by applying to the eyes of a patient being treated a compound selected from the group consisting of hydrocortisone, medrysone, prednisolone, dexamethasone, fluoromethasone, rimexolone, and loteprednol ebonate, and combinations of these compounds with other constituents.

24 Claims, 2 Drawing Sheets

METHODS OF TREATING HEADACHE AND FUNCTIONAL EXTRAOCULAR AND INTRAOCULAR MYOTENDINITIS

This application claims the benefit of U.S. Provisional Application Nos.: 60/034,103 filed Dec. 31, 1996 and 60/038,085 filed Feb. 18, 1997.

BACKGROUND OF THE INVENTION

1. Field of the Invention

My present invention provides two novel modes of administration of treatment media for treating headache and functional extraocular and intraocular myotendinitis, as distinct from infectious, e.g., viral, bacterial or fungal extraocular and intraocular myotendinitis, or from an auto-immune disease or other systemic disease.

The term "headache" is used herein to denote all eye-related headaches derived either from extraocular or an intraocular myotendinitis, and/or certain other categories of headache including vascular headache, non-eye-related tension headache and trigeminal neuralgia.

The term "ocular" is used herein in its broadest acceptation to denote the outer tunic of the human eye and all parts of the human eye contained therein.

The term "intraocular myotendinitis" is used herein to denote myotendinitis, myositis or fascitis (ed.g., inflamed or otherwise painful conditions) of the internal tissues of the human eye located within the ciliary body including the ciliary muscle(s) and ciliary tendon and any tissue attached thereto.

The term "extraocular myotendinitis" is used herein to denote myotendinitis, myositis, fascitis (e.g., inflamed or otherwise painful conditions) of the external tissues of the human eye located between the outer tunic of the eyeball and the bony orbit thereof).

SUMMARY OF THE INVENTION

It is an object of my present invention to provide novel methods of treatment for headache, and for functional extraocular and intraocular myotendinitis.

It is another object of my present invention to provide methods of treatment which achieve the above object, and do so with great rapidity.

It is a further object of my present invention to provide methods of treatment which achieve at least the first above-said object and include the testing of the binocular status of the patient's eyes in a plurality of different directions of gaze.

Other objects of my present invention will in part be obvious and will in part appear hereinafter.

My present invention, accordingly, comprises the several steps and the relation of one or more of such steps to each of the others, all as exemplified in the following disclosure, and the scope of my invention will be indicated in the appended claims.

A principal feature of my present invention is the novel mode of eye-related headache and functional ocular myotendinitis treatment of my present invention which takes advantage of the fact that the ophthalmic vein and artery communicate with cerebral blood vessels which are sometimes said to be the site or sites of certain types of headache, e.g., vascular headaches.

Since this access route to said cerebral blood vessels bypasses the blood-brain barrier, treatment media can be delivered to said cerebral blood vessels via this route without being blocked by the blood-brain barrier.

Another principal feature of my present invention is my discovery that certain steroidal drugs can be delivered to said cerebral blood vessels via this route, which originates at the surfaces of the eyes and proceeds via the conjunctival blood vessels, as witnessed by the fact that these drugs, when so administered, substantially or completely relieve headaches of the type which are associated in the literature with said cerebral blood vessels.

I believe that non-steroids (NSAIDS), and possibly anti-migraine drugs (vasoconstrictors, beta-blockers, and calcium channel blockers) may also be deliverable to these headache sites, and particularly to the anterior cerebral artery, by the delivery route of my invention.

It is to be understood that said first novel mode of headache treatment media delivery is a principal feature of my present invention.

Said second novel mode of headache and myotendinitis treatment, which takes advantage of the conjunctival blood vessels and their interconnections to extraocular myotendinous tissue, also takes advantage of the interconnection of the ophthalmic blood vessels and said cerebral blood vessels, is also a principal feature of my present invention, and will now be described in detail.

It is also to be understood that this second novel mode of treatment of my present invention, which is another principal feature of my invention, is in some ways more significant than the above-described first mode, in that it directly addresses the cause of the type of headache associated with said cerebral arteries, i.e., extraocular myotendinitis, and is not simply palliative.

For a fuller understanding of the nature and objects of the present invention reference should be had to the following detailed description, taken in connection with the accompanying drawings.

DESCRIPTION OF THE PREFERRED EMBODIMENTS

In general, the study of the nature and function of the eye muscles has been substantially neglected, and is sparsely represented in the ophthamalogical literature.

The literature relating to the nature and functioning of the eye muscles is largely devoted to studies relating to the gross weaknesses and imbalances of the eye muscles, with occasional references to headaches produced by attempts to achieve binocular fusion. Much of this literature, relating to headaches resulting from attempted binocular fusion, dates back as much as 60 to 80 years, and does not satisfactorily explicate the connection between eye muscle functioning and headache.

In order to explore the actual relationship between eye muscle functioning and headache I have repeatedly, with many patients, tested the binocular status of the patient's eyes in all directions of gaze, and not just straight ahead, as is the common practice.

To gain substantial understanding of the interplay between the twelve extraocular muscles, I have also found it necessary to compare, in many patients, the interaction of the extraocular muscles, and particularly the interplay of the horizontal, vertical and cyclotorsional movements thereof.

Figure 2:
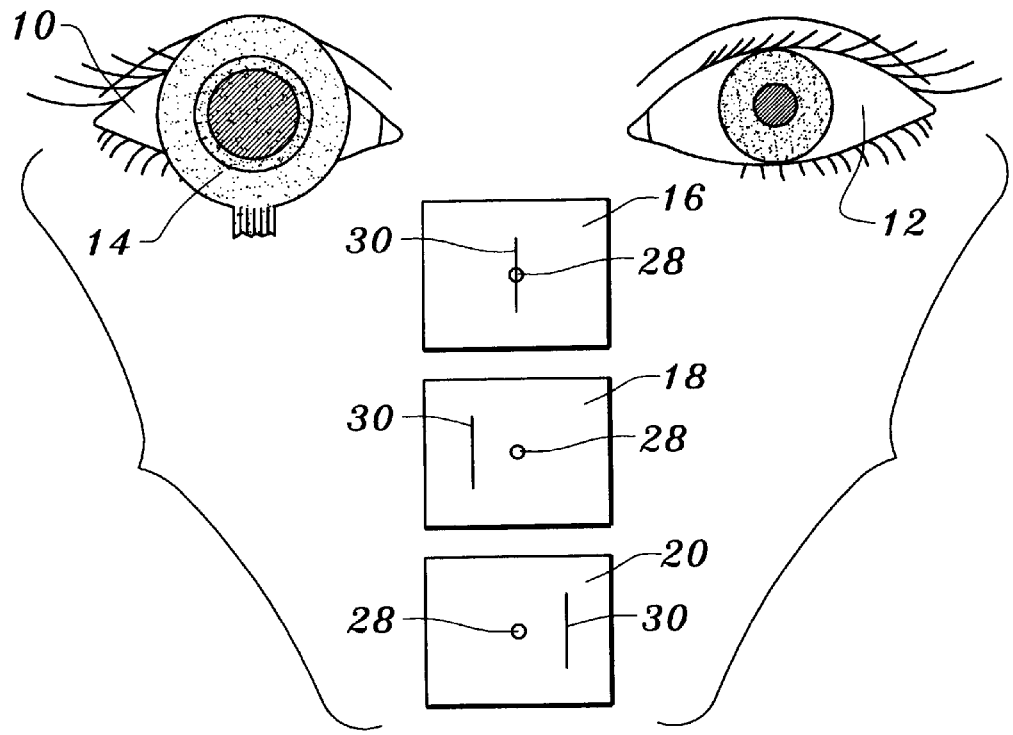
FIGS. 2 and 2A are schematic representations of certain features of the Red Maddox testing procedure which is utilized in determining the position of rest of the patient's eye muscles in certain procedures of my present invention.
Figure 2A:
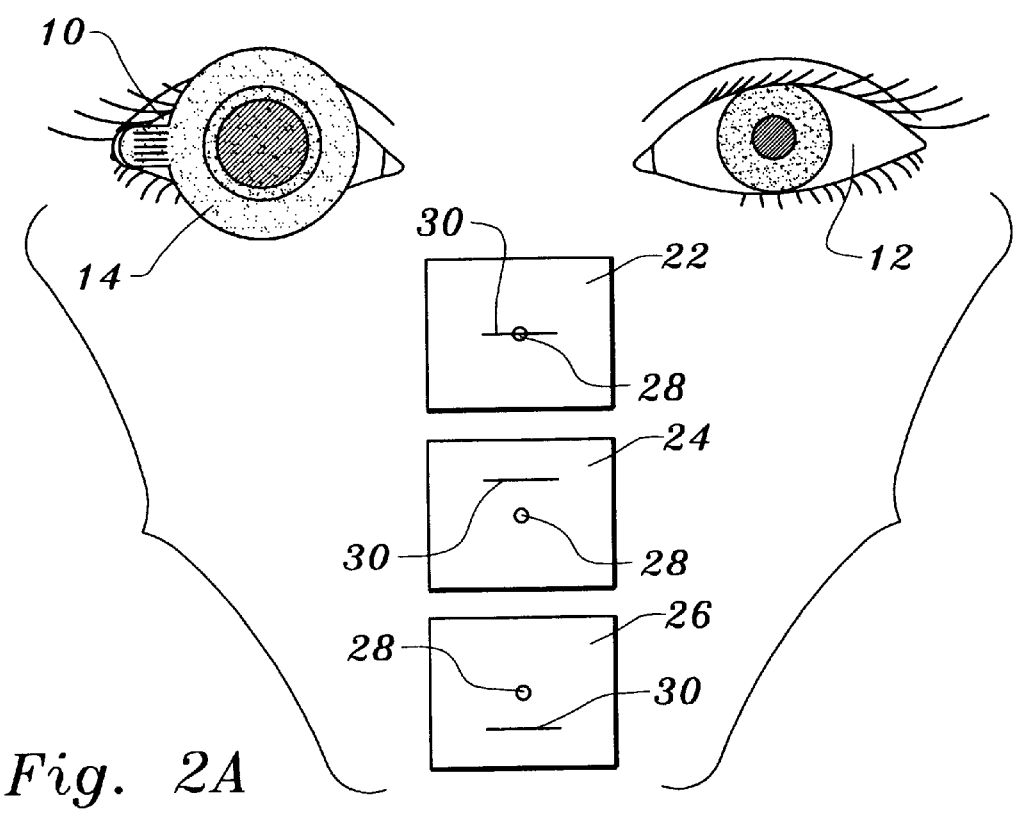

My studies of these extraocular muscle relationships was accomplished by making use of the Red Maddox rod test, which is a test utilizing a striated red filter 14, FIGS. 2 and 2A. This red filter disrupts binocular vision when light which has passed therethrough is impinged upon one eye of a patient and is perceived as a red line 30, FIGS. 2 and 2A, while the other eye perceives the light 28. The separation of the red and white images during this Red Maddox testing procedure indicates the horizontal and vertical positions of rest of the eye muscles (See FIGS. 2 and 2A). When this light is maintained in different orientations with respect to the eyes being tested (16, 18, 20, 22, 24, 26) it becomes possible to determine whether these eyes are turning in or out and up or down, and generally how the eye muscles are behaving.

Referring now to FIGS. 2 and 2A, it will be understood by those having ordinary skill in the vision-related arts that FIG. 2 relates to the location of the horizontal position of rest of the patient's eyes, and that FIG. 2A relates to the location of the vertical position of rest of the same patient's eyes.

In the figures are shown the patient's right eye 10 and left eye 12.

As also seen in these figures a Red Maddox filter 14 is located, in both figures, before the patient's right eye.

In each FIGS. (2 and 2A) the vertical array of "boxes" 16, 18, 20, 22, 24, 26 contain, respectively, a representation of various binocular arrangements of each eyes' perceived image at a particular stage of my below described test.

In FIGS. 16 and 22 the conjunction of the perceived light image 28 of the patient's left eye and the right eye 30 indicates that in a state of rest the eyes are aimed the same direction, also known as orthophoria. FIG. 16 illustrates horizontal orthophoria and FIG. 22 depicts vertical orthophoria (cyclofusional orthophoria is not shown).

The information about the eyes being tested which is derived by means of the Red Maddox rod test (FIGS. 2 and 2A), taken with the results of certain binocular eye testing procedures of my present invention, makes it possible to determine which extraocular muscles are straining during the testing procedure.

Said particular binocular eye testing procedures are modifications of the well known Turville Infinity Balance (TIB) test, which allows an observer to see right eye and left eye images independently while both eyes are open, and to see peripheral images binocularly at the same time.

The conventional method employed in the TIB test is to place a septum between two letters seen in the examining room mirror, so that each of these two letters is seen monocularly (the right eye does not see the image presented to the left eye, and vice versa).

The observer then translates his or her gaze in the direction of greatest eye muscle imbalance, and may thus see that the image perceived by one eye becomes blurred. As an example, in a subject with a weak superior oblique muscle of the right eye the greatest eye muscle imbalance is in the direction in which said muscle has its greatest action, namely, lower left gaze. Thus, depending on which eye compensates for the imbalance, that eye will blur increasingly as the head is raised, turned and tilted to the right during the TIB test. In this example, then, the MBE is greatest in the lower left direction of view. It is important to keep in mind that as the strain increases, the blur increases.

To confirm that the blur occurs during the use of both eyes in their attempts to maintain binocular fusion, the non-blurred other eye is covered. I have observed that when the other eye is covered, and thus binocular vision is prevented, the strain in said one eye disappears and the letter displayed to said one eye is clearly seen. If the blur disappears, then it can be assumed that the stress in the extraocular muscles trying to maintain binocular fusion is eliminated.

I call this new phenomenon, which I have discovered, the monocular blur effect (MBE). (See the appended copy of my paper entitled "The Association of Headache and Monocular, Blur Effect in a Clinical Population", *Optometry and Vision Science*, Vol. 17, No. 11, pp. 707–712, Appendix A).

The MBE confirms the straining of one eye during the act of binocular vision.

The importance of the MBE to this invention is that the variable blur indicates the presence of extraocular muscular straining and ensuing headache, both usually occurring on the same side of the head. Two factors, the difficulty overcoming the fusional error and amount of time exerting the eyes, can work together to produce such a stress on the extraocular muscles that the tendons, tethered as Tenon's capsule, become afflicted. The constant pull and strain of the eye muscles inflames the tendons aggravating the onset of headache and in bad cases migraine.

The neuronal activity maintaining this abnormal oculo-motor system releases biochemicals into the cerebral arterial flow. Experts believe that they are responsible for the cascade of events that lead to trigeminal neuralgia and possibly migraine.

The auras associated with true migraine and customarily explained as the dilation of cerebral arteries may at times be the visual effect of an inflamed tendon irritating the retina at the same location as the tendon but inside the eye and eliciting visual phenomena projected in predictable directions.

Other observations made during the modified TIB test are (1) increasing vertical fixation disparity and (2) increasing aneisokonia, or difference in image size; both of which occur while performing the test in the direction of increasing muscle imbalance.

Another observation heretofore unrecognized in all ophthalmological literature is the variation of perceived depth perception that corroborates variable binocular error. Specifically, using a standard depth perception test such as the well-known Stereo Fly test, the subject will perceive diminished depth perception in the direction of weakness revealed by the modified TIB test. In the aforementioned example, then, the subject would notice reduced depth perception in the lower left corner of gaze.

I have also observed transient monocular astigmatism associated with this strain. Here, it might be assumed that the extraocular eye muscles are straining to the degree that the shape of the eyeball is affected. In particular the axis of the astigmatism can shift dramatically.

Finally, all of the observations are substantiated by the subject's ability to actually feel the strain of the eyes physically and visually when viewed targets are moved in the direction of greatest difficulty. At times, the binocular error is felt to be greatest in up and down gaze or side to side. In most instances, however, the greatest and least error occur along a diagonal direction, e.g., in the aforementioned example, least error in upper right and greatest error in lower left gaze.

The abovedescribed tests, i.e., the Red Maddox and the modified TIE test (or Turville-Sucher Test (TST)), when utilized jointly in accordance with the principles of my present invention described hereinabove, clearly indicate the source of vision blurring experienced by the testee during the Turville-Sucher Test. That is to say, there is little if anything else to account for this vision blurring, variable fixation disparity, variable aneisokonia, variable depth perception and variable sensation of strain, other than the eye muscles which are the only anatomical element which changes when the eyes gaze in different directions.

I have also discovered that when an eye muscle imbalance pattern is detected by the combination of vision tests of my present invention described hereinabove it is possible to confirm said resulting eye strain by means of digital palpation. Palpating the globe finalizes the diagnosis of extraocular myotendinitis. Digital palpation elicits pain by utilizing a small amount of pressure from the fingertip while lightly touching the globe as best as possible near the equator.

Figure 1:
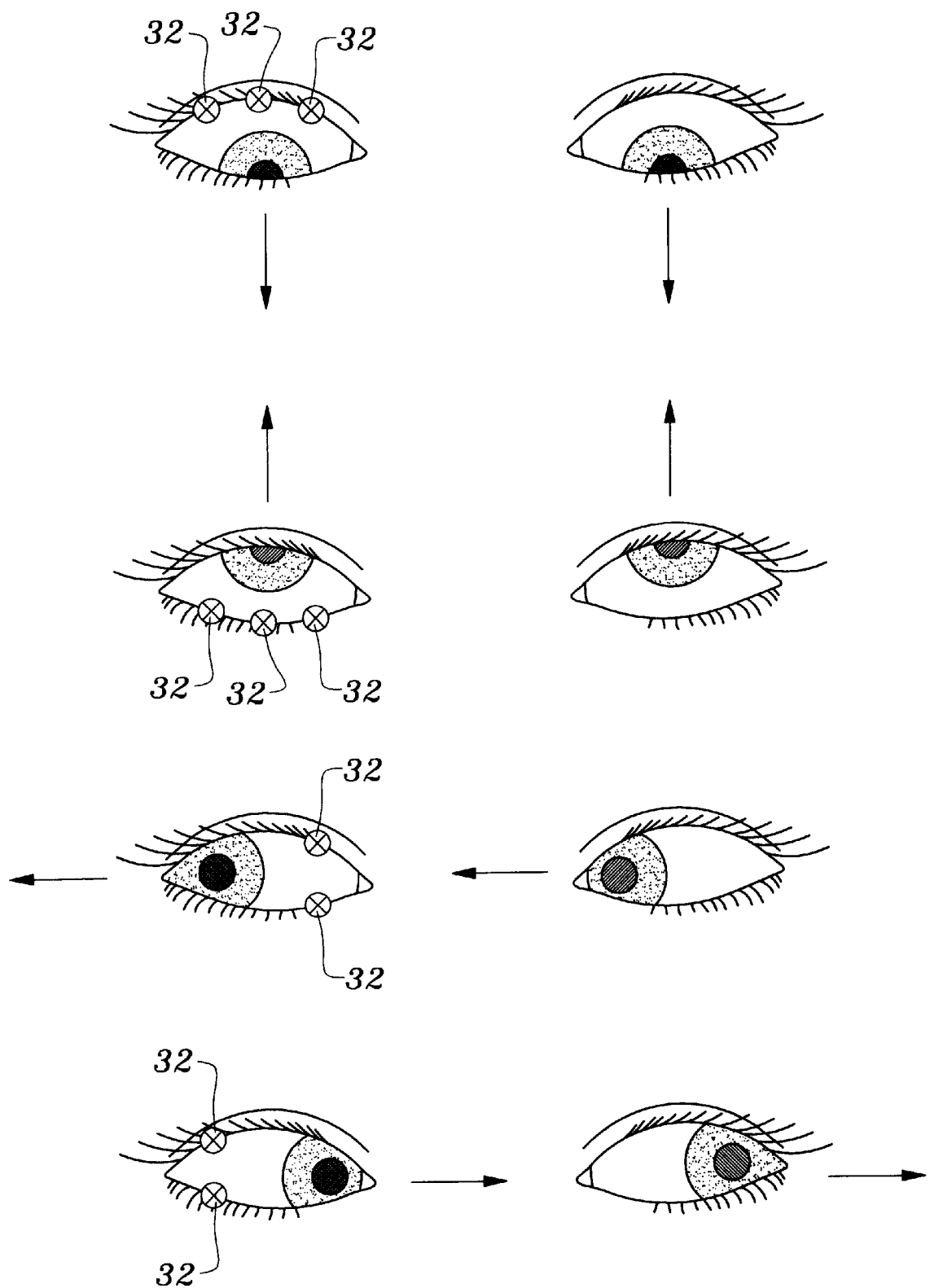
FIG. 1 is a palpation point diagram showing the palpation points employed in certain treatment methods of my invention.

By palpating the points of insertion of the eye muscles (32, FIG. 1), the observer can detect tenderness and soreness (FIG. 1). These points of tenderness and soreness occur in predictable configurations with regard to the eye strain patterns. If, in the aforementioned example of the weak superior oblique, when MBE occurs in the right eye and the Red Maddox test indicates over-converging, then the tender spot will occur on the outside of the right eye. These tender spots can vary in intensity in accordance with the temporal proximity of a headache to the time of testing. If the test is carried out during a headache of the related type these tender spots will become very sore and quite sensitive to the touch. In the case of migraine these insertion tendons can become extremely sensitive.

Once it has been determined that such tender areas exist adjacent to the eyes near the extraocular muscle tendon insertions and that they correspond to eye muscle imbalance discovered by means of the above-described test combination of my present invention, diagnoses of extraocular myotendinitis specifically due to an eye muscle imbalance can be confidently made.

The use of compounds that not only produce quick anesthesia, but also reduce the inflammation due to myotendinitis and eye muscle strain and provide immediate relief of headache (within one to ten minutes) confirms the relation of headache and extraocular myotendinitis and eyestrain. Migraine may require a longer recovery time and more timely applications due to its broader devastating effects and other origins of that kind of headache; however, the earlier the treatment the easier to abort this variety of headache. Relieving the eye component of migraine may rid the pain successfully, but more than likely it will become another weapon to fight off the paroxysms of pain that accompany migraine.

Among the pharmaceutical agents of my present invention which have been found to relieve extraocular myotendinitis and accompanying headache the best are hydrocortisone, medrysone, prednisolone, dexamethasone, florometalone, rimexolone and loteprednol. There are two derivatives of fluoromethalone, the alcohol and the acetate, two derivatives of prednisolone, the acetate and sodium phosphate and two derivatives of dexamethasone, the alcohol and sodium phospate. In addition, there are combinations of these agents with antibiotics. These combinations may also have the desired effect of relieving pain from extraocular myotendinitis. There are sulfacetamide-steroid combinations such as Blephamide, Isoptocetapred, Vasocidin, AK-Cide, and FML-S. Other antibiotic-steroids include Polypred, Pred-G, Maxitrol, Cexacidin, Neodecadron, Tobradex, Cortisporin and Metimyd.

The application of the corticosteroid drops requires only 1–2 drop(s) in the affected eye(s). If the pain is particularly intense and still present with palpation after the initial therapy, another instillation of drop(s) can be added five to ten minutes later.

The corticosteroids have two desired effects—a short term effect and a long term effect. The initial cessation of pain that occurs quickly is due to their direct-acting (non-genomic) anesthetic effect which blocks neuronal signals of pain. The intracellular (genomic) indirect-acting, anti-inflammatory effect, which takes longer, reduces the production of irritating hydrolytic enzyme compounds such as prostaglandins, leukotrienes, thromboxanes, histamines and others. After the initial anesthesia, the anti-inflammatory effect acts to prolong the reduction of pain.

In a recent clinical study of sixty patients with detectable sore areas around the eyes, one drop of saline was used to determine any placebo effect and then one drop of either prednisolone acetate or prednisolone phosphate was placed in the eyes. Only ten subjects had a placebo effect that lasted greater than ten minutes although nearly half of the subjects experienced temporary comfort (1–2 minutes) with the saline drop. Of the remaining 50 subjects, 25 received the prednisolone acetate and 25 prednisolone sodium phosphate, 43 experienced significant relief of pain within five to ten minutes (on a scale of four a subjective improvement of two levels, e.g., a rating of 4, very sore, would have to come down to a rating of 2 to be significant). Subsequently, 39 of these 43 treated subjects felt prolonged relief 60 minutes after the drug instillation. This clinical study shows a significant effect of both the prednisolone acetate and the prednisolone sodium phosphate on the resolution of eye pain from functional extraocular myotendinitis. Eliminating the placebo effect, the corticosteroid had a 78% positive result, 14% had no effect and 8% only experienced temporary relief. A lasting placebo effect occurred in 16% and 45% had a temporary placebo effect.

Because a known percentage of individuals are steroid responders who manifest increasing intraocular pressure due to long term use of steroids, the hydrophilic derivatives, which do not penetrate the eye readily but do act effectively at the external myotendinous tissues and the receptor sites therein, are recommended for therapeutic use. If, however, it is determined that an intraocular myotendinitis due to accommodative tension exists, then the lipophilic derivatives are more effective.

It has also been noted that certain non-steroidal anti-inflammatory agents are effective to at least some extent in the treatment regimens of my present invention, though of considerably lesser efficacy than some of the agents mentioned hereinabove. Among these non-steroidal anti-inflammatory agents are kertorlac tromethamine, flurobiprofen, suprofen and diclofenac.

It is to be particularly noted, however, that none of the above-discussed pharmaceutical agents has been previously indicated in the literature to be of value in the reduction of eye muscle imbalance, or the reduction of headache resulting from eye muscle imbalance. In fact, most ophthalmologists dispute the sometimes heard contention that headaches are produced by eye muscle imbalance and eye muscles are hardly ever linked to migraines.

However, the treatment regimens and agents of my present invention discussed above are clearly not obvious, as witnessed by the fact that although most of the above-listed therapeutic agents have been available for many years, none of them are currently used for the treatment of headache due to eye muscle imbalance. Also, headache has been treated successfully in patients who were not successfully treated by other modalities.

As will now be evident to those having ordinary skill in the ophthalmological art, informed by the present disclosure, the treatment regimens of my present invention are comprised of the step of applying eye drops of one of the above-listed therapeutic agents, or a combination thereof, alone or in a vehicle or diluent, to the surfaces of the patient's eyes.

Thus, for example, a treatment regimen of my present invention may comprise the application of eyedrops of my invention, as described above, to either the affected eye or both, or the affected side of the headache or both, and to repeat this application as necessary.

In the case of ocular stress syndrome, which occurs widely among computer users, the application of only one or two drops in the affected eye is all that is needed to produce substantially complete pain relief.

The packaging of said invention should be single dose dispensers of non-preserved solution or suspension so as to promote compliance and to avoid allergic reactions to preservatives. Commercially, perhaps there would be a dozen single dose dispensers in each package.

The treatment regimen of my present invention is probably the first breakthrough in understanding the deluge of complaints about eye strain and sore eyes which are constantly plaguing computer users and causing recurring headaches.

The treatment regimens of my present invention, i.e., the use of ocular pharmaceutical agents to quell and relieve headache and migraine, has significantly aided individuals who were not helped by any other medications and treatment regimens. It is to be understood, of course, that the causes of headaches are polyfactorial, and that not all headaches result from eye muscle imbalance or overuse of the eye muscle. In the computer-impacted world of today, however, many headaches result from eye muscle imbalance, and it is believed that the treatment regimens of the present invention will thus provide new hope for many headache sufferers.

All of the topical ophthalmic steroids seem to work to resolve the pain of myotendinitis, but the most clinically useful steroids are those which do not penetrate the globe of the eye. These are derivatives that are hydrophilic or water soluble. The lipophilic compounds can penetrate the lipid soluble corneal epithelium so that internal inflammations can be quelled. With penetration of the eye, however, the steroid can increase intraocular pressure and cause cataract. Of all of the ophthalmic steroids, the phosphate form of prednisolone which can not penetrate the eye readily would be considered the drug of choice in treating extraocular myotendinitis, since it is an external condition not requiring ocular penetration.

As a part of the present invention it is recognized that these steroids have bi-phasic properties, i.e., the quick, direct-acting anesthetic and the slower, genomically-expressed anti-inflammatory phases. The former is what knocks out the pain from myotendinitis within a single minute or sooner. Apparently, it attaches to the receptors responsible for sending the pain signal to the brain. The slower acting anti-inflammatory effect occurs one to three hours after instillation and prolongs the resolution of pain. This effect is classical and well-known, whereas the anesthetic effect is unknown and has never been used in any eye conditions.

It will thus be seen that the objects set forth above, among those made apparent from the preceding description, are efficiently attained, and since certain changes may be made in the above constructions and the methods carried out thereby without departing from the scope of the present invention it is intended that all matter contained in the above description or shown in the accompanying drawings shall be interpreted as illustrative only, and not in a limiting sense.

It is also to be understood that the following claims are intended to cover all of the generic and specific features of the invention hereindescribed, and all statements of the scope of the invention which, as a matter of language, might be said to fall therebetween.

What is claimed is:

1. A method for treating headache due to functional ocular myotendinitis, comprising the step of applying to at least one eye of a patient a therapeutically effective amount of a compound having anesthetic and anti-inflammatory properties.

2. The method of claim 1, wherein said compound is selected from the group consisting of hydrocortisone, medrysone, prednisolone, dexamethesone, fluoromethalone, rimexolone, and loteprednol ebonate.

3. The method of claim 1, wherein said compound is selected from the group consisting of the alcohol and the sodium phosphate derivatives of dexamethasone, the acetate and the sodium phosphate derivatives of prednisolone, and the alcohol and the acetate derivatives of fluoromethalone.

4. The method of claim 1, wherein said compound is selected from the group consisting of Blephamide, Isoptocetapred, Vasocidin, AK-cide, Metimyd, Optimyd, Sulfrin, Predsulfair, and FML-S.

5. The method of claim 1, wherein said compound is selected from the group consisting of Polypred, Pred-G, Maxitrol, Dexacidin, Neodecadron, Tobradex, and Cortispor.

6. The method of claim 1, wherein said compound is selected from the group consisting of Sumitryptan, Verapamil, and Atenolol.

7. A method for treating headache due to functional extraocular myotendinitis, comprising the step of applying to at least one eye of a patient a therapeutically effective amount of a compound having anesthetic and anti-inflammatory properties.

8. The method of claim 7, wherein said compound is selected from the group consisting of hydrocortisone, medrysone, prednisolone, dexamethesone, fluoromethalone, rimexolone, and loteprednol ebonate.

9. The method claim 7, wherein said compound is selected from the group consisting of the alcohol and the sodium phosphate derivatives of dexamethasone, the acetate and the sodium phosphate derivatives of prednisolone, and the alcohol and the acetate derivatives of fluoromethalone.

10. The method of claim 7, wherein said compound is selected from the group consisting of Blephamide, Isoptocetapred, Vasocidin, AK-cide, Metimyd, Optimyd, Sulfrin, Predsulfair, and FML-S.

11. The method of claim 7, wherein said compound is selected from the group consisting of Polypred, Pred-G, Maxitrol, Dexacidin, Neodecadron, Tobradex, and Cortispor.

12. The method of claim 7, wherein said compound is selected from the group consisting of Sumitryptan, Verapamil, and Atenolol.

13. The method of claim 7, wherein said compound is selected from the group consisting of kertorlac tromethamine, fluorbiprofen, suprofen, and diclofenac.

14. A method for treating headache due to functional intraocular myotendinitis, comprising the step of applying to at least one eye of a patient a therapeutically effective amount of a compound having anesthetic and anti-inflammatory properties.

15. The method of claim 14, wherein said compound is selected from the group consisting of hydrocortisone, medrysone, prednisolone, dexamethesone, fluoromethalone, rimexolone, and loteprednol ebonate.

16. The method of claim 14, wherein said compound is selected from the group consisting of the alcohol and the sodium phosphate derivatives of dexamethasone, the acetate and the sodium phosphate derivatives of prednisolone, and the alcohol and the acetate derivatives of fluromethalone.

17. The method of claim 14, wherein said compound is selected from the group consisting of Blephamide, Isopto-cetapred, Vasocidin, AK-cide, Metimyd, Optimyd, Sulfrin, Predsulfair, and FML-S.

18. The method of claim 14, wherein said compound is selected from the group consisting of Polypred, Pred-G, Maxitrol, Dexacidin, Neodecadron, Tobradex, and Cortispor.

19. The method of claim 14, wherein said compound is selected from the group consisting of Sumitryptan, Verapamil, and Atenolol.

20. A method for treating headache due to functional ocular myotendinitis, comprising the steps of:

determining the presence of functional ocular myotendinitis by physical exam of the eyes of a patient, and, when functional ocular myotendinitis is found, applying to at least one eye of the patient a therapeutically effective amount of a compound having anesthetic and anti-inflammatory properties.

21. The method of claim 20, wherein said step of physical exam includes the step of applying a modified Turville Infinity Balance test to manifest the monocular blur effect.

22. The method of claim 20, wherein said step of physical exam includes the step of determining the position of rest of the patient's eye muscles by applying the Red Maddox rod test, and thereafter applying a modified Turville Infinity Balance test to manifest the monocular blur effect.

23. The method of claim 20, wherein said step of physical exam includes the steps of palpating the globe of each eye of the patient close to the center of each globe to determine the presence of inflammation indicative of functional ocular myotendinitis.

24. The method of claim 20, wherein said step of physical exam includes the initial step of testing the binocular status of the patient's eyes in a plurality of different directions of gaze.

* * * * *